United States Patent [19]

Paul et al.

[11] 4,107,308

[45] Aug. 15, 1978

[54] IMIDAZO[1,5-d]-AS-TRIAZINES

[75] Inventors: Rolf Paul, River Vale, N.J.; Judith Menschik, Tappan, N.Y.

[73] Assignee: American Cyanamid Company, Stamford, Conn.

[21] Appl. No.: 843,175

[22] Filed: Oct. 18, 1977

[51] Int. Cl.$^2$ .............. C07D 253/08; C07D 487/04; A61K 31/53

[52] U.S. Cl. ...................... 424/249; 71/93; 544/184

[58] Field of Search ................ 544/184; 424/249

[56] References Cited

U.S. PATENT DOCUMENTS

| | | | |
|---|---|---|---|
| 2,837,520 | 6/1958 | Fusco et al. | 544/184 |
| 3,840,537 | 10/1974 | Garside et al. | 544/184 |

*Primary Examiner*—John M. Ford
*Attorney, Agent, or Firm*—Harry H. Kline

[57] ABSTRACT

There are provided novel substituted imidazo-[1,5-d]-as-triazines useful as hypotensive agents as well as exhibiting herbicidal activity.

18 Claims, No Drawings

IMIDAZO[1,5-d]-AS-TRIAZINES

This application is a continuation-in-part of our copending applicaton, Ser. No. 765,336, filed Feb. 3, 1977, now abandoned.

BRIEF SUMMARY OF THE INVENTION

This invention relates to new organic compounds and, more particularly, is concerned with novel substituted imidazo[1,5-d]-as-triazines which may be represented by the following structural formula:

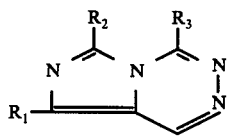

wherein $R_1$ is hydrogen, alkyl having up to 4 carbon atoms, chlorine, or bromine; $R_2$ is hydrogen, alkyl having up to 4 carbon atoms, methoxymethyl or phenyl; and $R_3$ is allylthio, pyrazolylamino, piperazinyl, 4-methylpiperazinyl, or moieties of the formulae: —S-R, —NH-R, or

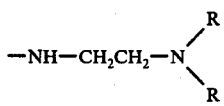

wherein R is alkyl having up to 3 carbon atoms. The invention also includes novel compositions of matter containing the above-defined compounds useful as hypotensive agents as well as exhibiting herbicidal activity and the method of meliorating hypertension in mammals therewith.

DETAILED DESCRIPTION OF THE INVENTION

The novel compounds of the present invention are generally obtainable as white to pale yellow crystalline materials having characteristic melting points and absorption spectra and which may be purified by recrystallization from common organic solvents such as methanol, ethanol, dimethylformamide, acetone, ethyl acetate, and the like. They are appreciably soluble in nonpolar organic solvents such as toluene, carbon tetrachloride, and the like and are relatively soluble in water. The organic bases of this invention wherein $R_3$ is a basic nitrogen containing moiety form non-toxic acid-addition salts with a variety of pharmacologically acceptable organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, citric, lactic, succinic, tartaric, benzoic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their non-toxic acid-addition salts.

The novel compounds of the present invention wherein $R_3$ is alkylthio may be readily prepared in accordance with the following reaction scheme:

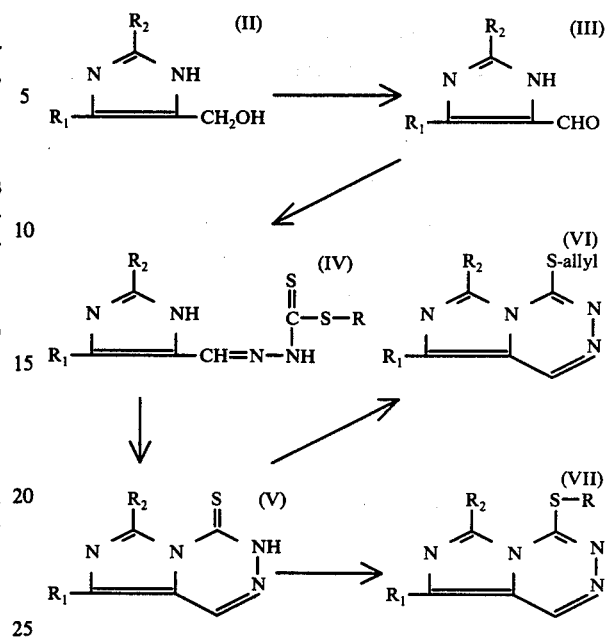

wherein R, $R_1$, and $R_2$ are as hereinabove defined. In accordance with the above reaction scheme, an appropriately substituted 4-imidazolemethanol (II) is oxidized with concentrated nitric acid to provide the corresponding 4-imidazolecarboxaldehyde (III). This oxidation is best carried out by suspending or dissolving each gram of starting material (II) in from about one ml. to about seven ml. of concentrated nitric acid and heating the reaction mixture at steam bath temperature for 2–3 hours. Alternatively, the reaction mixture may first be allowed to stand at room temperature for 8–16 hours and then heated for a short time (15–30 minutes) on the steam bath. The resulting reaction solution is preferably first diluted with water and then neutralized with any convenient base such as caustic, soda ash, or concentrated aqueous ammonia. The precipitated product (III) is removed, washed with water, and purified by recrystallization from common organic solvents such as ethyl acetate, ethanol, and the like. Alternatively, the 4-imidazolemethanol (II) may be oxidized with manganese dioxide in chloroform or tetrahydrofuran at the reflux temperature for a period of 4–6 hours to provide the 4-imidazolecarboxaldehyde (III).

The 4-imidazolecarboxaldehyde (III) may be readily converted to the 3-(4-imidazolymethylene)dithiocarbazic acid ester (IV) by treatment with an alkyl dithiocarbazinate of the formula $H_2N$-NH-$CS_2$-R. This condensation is conveniently carried out in a lower alkanol solvent containing a few drops of glacial acetic acid at a temperature of 25°–75° C. whereupon the product (IV) forms almost immediately and is removed by filtration. Cyclization of the 3-(4-imidazolylmethylene)dithiocarbazic acid ester (IV) is readily accomplished by heating in a non-polar high boiling organic solvent such as diphenyl ether at 175°–275° C. for 15–30 minutes whereby the corresponding imidazo[1,5-d]-as-triazine-4(3H)-thione (V) is obtained. Conversion of the thiones (V) to the 4-allylthio-(VI) and 4-alkylthio- (VII) imidazo[1,5-d]-as-triazines is accomplished by first dissolving the thione (V) in a lower alkanol such as methanol or ethanol and adding an equimolar excess of sodium or sodium methoxide to the solution at room temperature.

Thereupon, an equimolar amount of allyl bromide or an alkyl iodide having up to 3 carbon atoms is added and the reaction mixture is either refluxed for about an hour or allowed to stand at room temperature overnight. The product (VI) or (VII) crystallizes from the reaction mixture upon cooling.

Alternatively, the thiones (V) may be obtained by heating the corresponding oxo compounds (IX) with phosphorus pentasulfide in an inert solvent as set forth in the following reaction scheme:

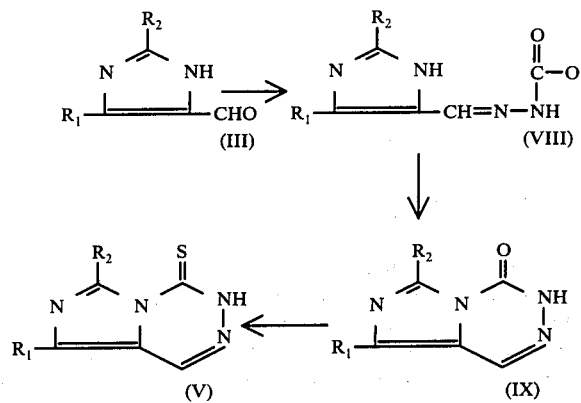

wherein R, $R_1$ and $R_2$ are hereinabove defined. This is a particularly convenient method when $R_1$ is halogen. The 4-imidazolecarboxaldehyde (III) may be readily converted to the 3-(4-imidazolylemethylene) carbazic acid ester (VIII) by treatment with an alkyl carbazate of the formula $H_2N-NH-CO_2-R$. This condensation is conveniently carried out in a lower alkanol solvent containing a few drops of glacial acetic acid at at temperature of 25°–75° C. whereupon the product (VIII) forms almost immediately and is removed by filtration. The cyclization of the 3-(4-imidazolylmethylene) carbazic acid ester (VIII) is readily accomplished by heating in a non-polar high boiling organic solvent such as diphenyl ether at 175°–275° C. for 15–30 minutes whereby the corresponding imidazo [1,5-d]-as-triazin-4(3H)-ones (IX) are obtained. The compounds (IX) wherein $R_1$ is chloro or bromo may be prepared by the chlorination or bromination, respectively, of the corresponding compounds (IX) wherein $R_1$ is hydrogen. This halogenation is accomplished by treating the starting materials with chlorine or bromine in an inert solvent such as chloroform or carbon tetrachloride at steam bath temperature.

The novel compounds of the present invention wherein $R_3$ is monoalkylamino may be readily prepared in accordance with the following reaction scheme:

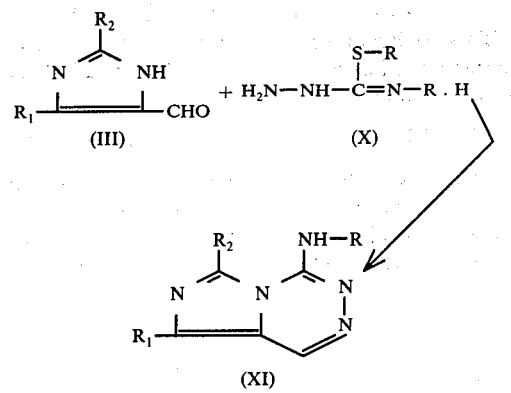

wherein R, $R_1$, and $R_2$ are as hereinabove defined. In accordance with the above reaction scheme, an appropriately substituted 4-imidazolecarboxaldehyde (III) is reacted with a 3,4-dialkylthiosemicarbazide hydroiodide (X) in a lower alkanol solvent at the reflux temperature for a period of time of from about 30 minutes to several hours or more. The reaction mixture is then concentrated to dryness in vacuo and the residue is redissolved in a lower alkanol containing an equimolar amount of sodium methoxide. This solution is also concentrated to dryness in vacuo and the residue is heated in a non-polar high boiling organic solvent such as diphenyl ether at 225°–275° C. for 15–30 minutes. The product (XI) separates from the reaction upon cooling to room temperature.

The novel compounds of the present invention wherein $R_3$ is pyrazolylamino, piperazinyl, 4-methylpiperazinyl or N,N-dialkylaminoethylamino may be readily prepared by treating an appropriately substituted 4-methylthio-imidazo[1,5-d]-as -triazine ($R_3$ is -SCH$_3$ is formula I) with a molar excess of 3-aminopyrazole, piperazine, 4-methylpiperazine, or an N,N-dialkylaminoethylamine. This condensation is best carried out in a non-polar organic solvent such as benzene or toluene at the reflux temperature for a period of time of from about 24 to about 48 hours. The product is obtained by evaporation of the solvent and recrystallization from an organic solvent such as dimethylformamide or a lower alkanol.

The novel compounds of the present invention possess anti-hypertensive activity at non-toxic doses and as such are useful as hypotensive agents. These compounds have been tested pharmacologically and found to have such properties with a desirable wide spread between does producing lowered blood pressure and toxic symptoms. In determining this effect of these compounds on hypertension, adult male, 16–20 weeks old, spontaneous hypertensive rats from Taconic Farms, Germantown, New York, weighing about 300 grams are used. The rats are dosed by gavage with the test compounds at the indicated dose in mg. per kg. of body weight. All doses of drug were suspended in 2% starch (2 ml./kg.). A second identical dose of the test compound is given at the 24th hour. The mean arterial blood pressure (MAP) of the conscious rats is measured directly by femoral artery puncture at the 28th hour. The results of this test with typical compounds of the present invention appear in Table I below.

Table I

| Compound | Dose (mg./kg.) | MAP (mm. Hg) 28th hour |
| --- | --- | --- |
| 4-methylamino-imidazo-[1,5-d]-as-triazine | 100 | 131 |
| 4-(3-pyrazolylamino)-imidazo[1,5-d]-as-triazine | 100 | 134 |
| Controls | vehicle | 166 |

Some of the novel compounds of the present invention are active in inhibiting the enzyme cyclic-AMP phosphodiesterase which is responsible for the metabolism of cyclic AMP. As such, they are useful in the treatment of psoriasis, a disease in which the epidermal cyclic AMP levels are reported to be decreased. Also as such, they are useful in the treatment of asthma, since elevated levels of cyclic AMP in most cells are reported to inhibit the release of histamine and other mediators and since elevated levels of cyclic AMP in bronchial smooth muscle are reported to cause bronchodilation. See Ann. Reports in Medicinal Chem., Vol. 10, 197 (1975).

The inhibition of phosphodiesterase is determined by the mouse skin and monkey lung phosphodiesterase (PDE) inhibition tests as follows:

(A) MOUSE SKIN INHIBITION

Preparation of Mouse Skin PDE

Hairless mice (Jackson Laboratories), 3–4 months old are killed by cervical dislocation and their skins removed. Epidermal slices are taken at a thickness of 0.2 mm. The slices are weighed and homogenized at 100 mg./ml. in ice-cold tris-HCl buffer (0.04M, pH 8, containing 0.005M $MgCl_2$). Homogenates are centrifuged at 17,000 x gravity for 30 minutes. The supernatants are divided into aliquots which are stored at −20° C. Dilutions of the PDE are made with tris-HCl buffer just prior to use.

Anion Exchange Resin

AG1-X2®, 200–400 mesh (a polystyrene anionic exchange resin 8% cross linked from Bio-Rad Lab.) is washed with 0.5N HCl, 0.5N NaOH, 0.5N HCl and repeatedly with double distilled water to pH 5. The resin is allowed to settle and 2 volumes of water are added to one volume of settled resin.

Purification of $^3$H Cyclic AMP $^3$H-Cyclic AMP (21 c/m mole, Schwarz-Mann Inc.) is purified by addition of 0.1 to 0.2 ml. of stock (in 50% ethanol) to 5 ml. of anion exchange resin and 0.4 ml. of tris-HCl buffer. The mixture is vortexed, centrifuged at 1200 × gravity for 5 minutes and the supernatant is discarded. The resin is washed in the same manner eight more times with two volumes of tris-HCl buffer. Resin bound $^3$H-cyclic AMP is eluted by two successive washings with 4 ml. of 0.025N HCl (resin pH = 2.0). After centrifugation, the pooled acid washes containing $^3$H-cyclic AMP are aliquoted and lyophilized. The material is stored dry at −20° C. and reconstituted with tris-HCl buffer just prior to use with a volume sufficient to give approximately 200,000 CPM/0.1 ml.

PDE Assay

PDE activity is measured by the method of W. J. Thompson and N. N. Appleman, Biochemistry 10, 311 (1971). Assays are conducted in 12 × 75 mm. polypropylene test tubes. The reaction mixture consists of $^3$H-cyclic AMP (200,000 CPM), unlabeled cyclic AMP, PDE (100 μg. protein) and test compounds which are prepared by dissolving the compounds in methanol at a concentration of 10 mg./ml and then dilution in tris-HCl buffer. Final concentration of the test compounds in the incubation mixture is 10 μg./ml. The total volume of the incubation mixture is increased to 0.4 ml. with tris-HCl buffer containing 3.75 millimoles of 2-mercaptoethanol. The enzyme is incubated for 10 minutes at room temperature in the presence of the test compounds or buffer prior to the addition of the mixture of $^3$H-cyclic AMP and unlabeled cyclic AMP. Reactions are run at 30° C. for 15 minutes and then terminated by immersing in acetone-dry ice until frozen, followed by boiling for 3 minutes. Tubes are cooled to room temperature. $^3$H-5' AMP, formed in the reaction is converted to $^3$H-adenosine by the addition of 0.1 ml. of a solution of 5'-nucleotidase [16 μg./ml. in double distilled water Crotalus venom (Sigma Chemicals)] to the tubes which are incubated for 20 minutes at room temperature. This reaction is ended by the addition of one ml. of ice cold, stirred resin slurry which binds charged nucleotides (including $^3$H-cyclic AMP) but not $^3$H-adenosine. Tubes are vortexed and immersed in an ice bath for 15 minutes and then centrifuged at 1200 × gravity for 5 minutes. A 0.5 ml. portion is taken from each, placed in liquid scintillation vials with 10 ml. of Ready-Solv VI (Beckman Ind.) and counted for radio activity. Assay "blanks", determined with assay buffer substituted for PDE are less than 1% of total $^3$H-cyclic AMP added when $^3$H-cyclic AMP is purified as indicated.

(B) MONKEY LUNG INHIBITION

Preparation of Monkey Lung Cyclic AMP Phosphodiesterase

Lung parenchyma of African green monkeys is homogenized in a Waring blender and centrifuged at 40,000 × gravity for 20 minutes. The supernatant is brought to 70% saturation of ammonium sulfate, centrifuged and the pellet redissolved and ialysed, before aliquoting and storage at −20° C.

Assay of Monkey Lung Phosphodiesterase

Phosphodiesterase is assayed by the method of Thompson and Appleman, ibid. An assay tube contains a 0.4 m. solution of the following: 45 mM tris-HCl buffer, pH 7.4, 6.25 mM $MgCl_2$, 0.1 mM dithioerythritol, $10^{-6}$ M cyclic AMP, 0.1 μCi [$^3$H]-cyclic AMP, and test compound at the desired concentration (usually 1 mM or 0.1 mM). Compounds not readily soluble in water are dissolved at 40 times the desired concentration in methanol, and diluted 20 times with water. If the compound is not dissolved at this time, it is suspended by sonication before being diluted 1:2 into the assay tube. In this case the activity of the enzyme in the presence of the compound is compared to a solvent control (2.5% methanol), although the solvent alone has negligible effect. The reaction is initiated by addition of enzyme and proceedes at 25° C. for 20 minutes. It is terminated by incubation at 100° C. for 2 minutes. The tubes are cooled to 25° C., 0.8 μg of 5'-nucleotidase (Crotolus adamantus toxin) is added to each and the tubes incubated at 25° C. for 30 minutes. A one milliliter suspension of Bio-Rad Labs. AGIX8 (about 0.5 ml. of settled resin) is added, the tubes centrifuged at 900 × gravity for 10 minutes and an aliquot of supernatant removed for scintillation counting. The inhibition by the test compound is calculated as:

$$\% \text{ of control} = \frac{\text{'compound'} - \text{'blank'}}{\text{'control'} - \text{'blank'}}$$

where 'compound' is the cpm in the presence of compound, 'control' is the cpm in the absence of compound, and 'blank' is the cpm in the absence of enzyme. Since this assay requires sequential hydrolysis of cyclic AMP to AMP (by phosphodiesterase) followed by hydrolysis of AMP to adenosine (by 5'-nucleotidase), a compound which profoundly inhibited nucleotidase would appear to inhibit phosphodiesterase. For this reason, control tubes which contained [$^3$H]-AMP instead of [$^3$H]-cyclic AMP are run in parallel. A correction of the apparent phosphodiesterase activity is made for the rare compound which inhibited the hydrolysis of AMP.

Criterion for Activity as Inhibotor of Skin (A) or Lung (B) Phosphodiesterase

A compound is considered active if it inhibits more than theophylline, that is, to 50% of control of 1 mM concentration of compound, or to 80% of control for 0.05 mM concentration of compound.

The results with these compounds on inhibition of phosphodiesterase are recorded in Table II below.

TABLE II

| Compound | Mouse Lung Phosphodiesterase (B) | Mouse Skin Phosphodiesterase (A) |
|---|---|---|
| 4-(2-dimethylaminoethylamino)-imidazo[1,5-d]-as-triazine | | Active |
| 4-(3-pyrazolylamino)-imidazo[1,5-d]-as-triazine | | Active |

The novel compounds of the present invention have thus been found to be highly useful for lowering elevated blood pressure in mammals when administered in amounts ranging from about 1.0 milligrams to about 25.0 mg. per kilogram of body weight per day. A preferred dosage regimen for optimum results would be from about 5.0 mg. to about 15.0 mg. per kilogram of body weight per day, and such dosage units are employed that a total of from about 0.35 gram to about 1.0 gram of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compounds may be administered in any convenient manner such as by the oral, intravenous, intramuscular, or subcutaneous routes, or by inhalation theraepy including aerosol sprays.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for exampoe, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous theraphy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 0.1 and 5.0 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, is may contain, in addition to materials of the above type, a liquid carrier such as a fatty oil.

Various other materials may be present as coatings or to otherwise modify the physical form of the dossage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

2-n-Propyl-4-imidazolemethanol

A mixture of 180 gm. of 1,3-dihydroxyacetone dimer, 245 gm. of butyramidine hydroxhloride and one liter of liquid ammonia are warmed to 60° C. for 5 hours in a bomb. The mixture is evaporated to dryness and the residue is stirred with 600 ml. of 2-propanol. The mixture is filtered and the filtrate is concentrated in vacuo. A 600 ml. portion of 50% saturated aqueous sodium carbonate is added and the mixture is extracted with three 150 ml. portions of tetrahydrofuran. The combined organic layers are washed with 330 ml. of saturated aqueous sodium carbonate. The organic layer is dried over anhydrous sodium sulfate and evaporated to dryness. The residue is twice recrystallized from acetone giving the product, m.p. 95°–101° C.

EXAMPLE 2

2,5-Dimethyl-4-imidazolemethanol hydrochloride

This product is prepared by the method of Imbach et al., Bull. Soc. Chim. France, 1971, 1052.

EXAMPLE 3

2-Methyl-4-imidazolemethanol

A 189 gm. portion of acetamidine hydrochloride and 180 gm. of 1,3-dihydroxyacetone are combined with one liter of liquid ammonia as described in Example 1, giving the desired product, m.p. 115°–117.5° C.

EXAMPLE 4

4,5-Dimethyl-2-n-propyl-2-imidazoline-4,5-diol hydrochloride

A 112.7 gm. portion of butyramidine hydrochloride is dissolved in 200 ml. of water. A 107 gm. portion of freshly distilled diacetyl is added and the mixture is stirred. The pH is adjusted to 6.5–7.0 with 2N NaOH and the solution is chilled. The desired product is collected as a solid, m.p. 104°–107° C.

EXAMPLE 5

5-Methyl-2-n-propyl-4-imidazolemethanol

The product from Example 4 is dissolved 900 ml. of water and 350 ml. of concentrated hydrochloride, heated on a steam bath for 5 hours and then chilled. The solution is concentrated in vacuo and a mixture of 100 ml. of acetone and 100 ml. of ethanol is added. The mixture is filtered. The filtrate is evaporated and the residue is dissolved in 50 ml. of water and neutralized with a concentrated solution of $K_2CO_3$, until bubbling ceases. The top layer is separated and combined with 5 ml. of methanol. On standing, a precipitate forms. The solid is collected and the filtrate is diluted with acetone to give a second precipitate which is also collected. The solids are combined and recrystallized from hot acetone giving the desired product, m.p 134°–136° C.

EXAMPLE 6

5-Methyl-4-imidazolemethanol

This product is prepared by the method of Ewins, J. Chem. Soc. 99, 2052 (1911).

EXAMPLE 7

2-tert-Butyl-4-imidazolemethanol

A mixture of 326 gm. of pivalimidic acid methyl ester hydrochloride and 193.5 gm. of 1,3-dihydroxyacetone in 2 liters of liquid ammonia are reacted as described in Example 1, giving the desired product, m.p. 212°–221° C.

EXAMPLE 8

2-tert-Butyl-5-methyl-4-imidazolemethanol

In a two liter, three-necked flask, equipped with a magnetic stirrer, drying tube and gas inlet tube, is put 200 gm. of trimethylacetonitrile, 250 ml. of methanol and 500 ml. of diethyl ether. Hydrochloride gas is bubbled in for 2 hours with stirring. The mixture is transferred to a beaker, ether is added and the beaker is covered and stored in a cold room overnight. A 500 ml. portion of ether is added and the solid is filtered and washed with ether, giving white crystals of pivalimidic acid methyl ester hydrochloride.

A 75 gm. portion of the above material is converted to methyl pivalimidate hydrochloride by the method of Brown and Evans, J. Chem. Soc. 1962, 4039.

A 61 gm. portion of this latter product is dissolved in 50 ml. of water with warming and then cooled to room temperature. A 38.3 gm. portion of freshly distilled diacetyl is added and the reaction is continued as described in Examples 4 and 5 giving the desired product as white crystals, m.p. 195.5°–196.5° C.

EXAMPLE 9

2-n-Propyl-4-imidazolecarboxaldehyde

A 108.6 gm. portion of 2-n-propyl-4-imidazolemethanol and 107 ml. of concentrated $HNO_3$ are heated on a steam bath for 2 ½ hours. Three drops of fuming $HNO_3$ are added during this time. The pH is adjusted to 8 with concentrated aqueous $Na_2CO_3$ and the mixture is cooled to 0° C. overnight. The solid is recovered, washed with water and recrystallized from a mixture of ethyl acetate and petroleum ether giving a yellow solid. Treatment of the mother liquor gives an additional tacky solid which is triturated with 2-propanol giving a second solid. These two solids are taken up in hot 2-propanol and recrystallized as a yellow solid. This solid is recrystallized from ethanol:water (1:1) giving yellow crystals, m.p. 103.5°–105.5° C.

EXAMPLE 10

2-n-Butyl-4-imidazolecarboxaldehyde

Following the general procedure of Example 9, 2-n-butyl-4-imidazolemethanol is converted to 2-n-butyl-4-imidazolecarboxaldehyde.

EXAMPLE 11

2,5-Dimethyl-4-imidazolecarboxaldehyde

A 42.2 gm. portion of 2,5-dimethyl-4-imidazolemethanol and 44.8 ml. of concentrated nitric acid are mixed. When the initial reaction subsides, the solution is heated on a steam bath for one hour. The reaction mixture is neutralized with concentrated aqueous sodium carbonate, then concentrated under vacuum. After leaching the residue with 150 ml. of hot ethanol several times, the combined organic solutions are concentrated under vacuum. Chromatographing the residual oil on silica gel gives a solid which is recrystallized from 2-propanol-ethyl acetate to give the desired product, m.p. 164.5°–166° C.

EXAMPLE 12

5-Methyl-4-imidazolecarboxaldehyde

This product is prepared by the method of Hubball and Pyman, J. Chem. Soc. 1928, 21.

EXAMPLE 13

2-Methyl-4-imidazolecarboxaldehyde

A 143.0 ml. portion of concentrated $HNO_3$ is added in two portions to 119.2 gm. of 2-methyl-4-imidazolemethanol, with cooling after the first portion, and reacted as described in Example 9, giving the desired product, m.p. 170°–176° C.

Alternatively, this product may be made by the methods of Streith et al., Bull. Soc. Chim. France, 4159 (1971) and also Abushanab et al., J. Org. Chem. 40, 3376 (1975).

EXAMPLE 14

5-Methyl-2-n-propyl-4-imidazolecarboxaldehyde

An 80 gm. portion of 5-methyl-2-n-propyl-4-imidazolemethanol is oxidized with 67.3 ml. of concentrated $HNO_3$. A second portion of 101.4 gm. of the above compound is oxidized with 77 ml. of the acid. The reaction mixtures are combined, neutralized and worked up as in Example 11, giving the desired product, m.p. 126°–129° C.

EXAMPLE 15

2-tert-Butyl-4-imidazolecarboxaldehyde

A 7.7 gm. portion of 2-tert-butyl-4-imidazolemethanol is added to 100 ml. of chloroform and 100 ml. of tetrahydrofuran and heated gently. A 25 gm. portion of manganese dioxide is added and the mixture is stirred and refluxed for 5½ hours. The reaction mixture is filtered while hot and the manganese dioxide is triturated with hot chloroform and filtered. The two filtrates are combined and evaporated and the solid residue is recrystallized from ethyl acetate giving the desired producgt as white crystals, m.p. 194°–195° C.

EXAMPLE 16

2-tert-Butyl-5-methyl-4-imidazolecarboxaldehyde

A 19.76 gm. portion of 2-tert-butyl-5-methyl-4-imidazolemethanol and 16.5 ml. of concentrated $HNO_3$ are reacted as described in Example 11 giving the desired product, m.p. 196°–198° C.

EXAMPLE 17

2-(4-Imidazolylmethylene)dithiocarbazic acid methyl ester

A 17.78 gm. portion of imidazole-4-carboxaldehyde (Pyman, J. Chem. Soc. 1916, 186) is dissolved in 200 ml. of hot ethanol. A hot solution of 24.4 gm. of methyl dithiocarbazinate [Audrieth et al., J. Organic Chemistry 19, 733 (1954)] in 50 ml. of ethanol is added. A precipitate forms immediately and the mixture is heated and stirred for about 10 minutes. The mixture is cooled to 0° C. The precipitate is collected giving yellow crystals, m.p. 259°–261° C.

EXAMPLE 18

3-(2-n-Propyl-4-imidazolylmethylene)dithiocarbazic acid methyl ester

A 60 gm. portion of 2-n-propyl-4-imidazolecarboxaldehyde and 53.7 gm. of methyl dithiocarbazinate are reacted as described in Example 17 giving the desired product, m.p. 95°–104° C.

EXAMPLE 19

3-(2-Methyl-4-imidazolyl-methylene)dithiocarbazic acid methyl ester

A 33 gm. portion of 2-methyl-4-imidazolecarboxaldehyde and 40.3 gm. of methyl dithiocarbazinate are reacted as described in Example 17 giving the desired product, m.p. 274°–279° C.

EXAMPLE 20

3-(5-Methyl-4-imidazolylmethylene)dithiocarbazic acid methyl ester

A 16 gm. portion of 5-methyl-4-imidazolecarboxaldehyde and 19.5 gm. of methyl dithiocarbazinate are reacted as described in Example 17 giving the desired product, m.p. 180° C. resolidifies 230°–260° C.

EXAMPLE 21

3-[(2,5-Dimethyl-4-imidazolyl)methylene]dithiocarbazic acid methyl ester

A 20 gm. portion of 2,5-dimethyl-4-imidazolecarboxaldehyde and 20.8 gm. of methyl dithiocarbazinate are reacted as described in Example 17 giving the desired product, m.p. 279°–281° C.

EXAMPLE 22

3-[(5-Methyl-2-n-propyl-4-imidazolyl)methylene]dithiocarbazic acid methyl ester

A 20 gm. portion of 5-methyl-2-n-propyl-4-imidazolecarboxaldehyde and 17.7 gm. of methyl dithiocarbazinate are reacted as described in Example 17 giving the desired product, m.p. 175°–179° C.

EXAMPLE 23

Imidazo[1,5-d]-as-triazine-4(3H)-thione

A suspension of 164.5 gm. of 3-(4-imidazolylmethylene)dithiocarbazic acid methyl ester in 1.2 liters of diphenyl ether is heated and stirred at 175° C. until the methylmercaptan evolution subsides (20 minutes). The precipitate obtained on cooling to room temperature is collected and washed with petroleum ether, then acetone. The precipitate is then slurried with 1.2 liters of boiling methanol and filtered while hot to give the desired product, m.p. 271°–273° C.

EXAMPLE 24

8-Methyl-imidazo[1,5-d]-as-triazine-4(3H)-thione

A suspension of 14.39 gm. of 3-(5-methyl-4-imidazolylmethylene)dithiocarbazic acid methyl ester in 100 ml. of diphenyl ether is reacted as described in Example 23 giving the desired product as yellow crystals, m.p. 262°–268° C.

EXAMPLE 25

6-n-Propyl-imidazo[1,5-d]-as-triazine-4(3H)-thione

A 102.2 gm. portion of 3-(2-n-propyl-4-imidazolylmethylene)dithiocarbazic acid methyl ester in 500 ml. of diphenyl ether is reacted as described in Example 23 giving the desired product as a white solid, m.p. 201.5°–203.5° C.

EXAMPLE 26

6,8-Dimethyl-imidazo[1,5-d]-as-triazine-4(3H)-thione

A mixture of 30.26 gm. of 3-[(2,5-dimethyl-4-imidazolyl)methylene]dithiocarbazic acid methyl ester and 125 ml. of diphenyl ether is reacted as described in Example 23 giving a solid which is the desired product, m.p. 287.5°–290° C.

EXAMPLE 27

8-Methyl-6-n-propyl-imidazo[1,5-d]-as-triazine-4(3H)-thione

A mixture of 32.12 gm. of 3-[(5-methyl-2-n-propyl-4-imidazolyl)methylene]dithiocarbazic acid methyl ester and 200 ml. of diphenyl ether is reacted as described in Example 23 giving the desired product, m.p. 183°–186° C.

EXAMPLE 28

6-Methyl-imidazo[1,5-d]-as-triazine-4(3H)-thione

A mixture of 53.9 gm. of 3-(2-methyl-4-imidazolylmethylene)dithiocarbazic acid methyl ester and 200 ml. of diphenyl ether is reacted as described in Example 23 giving the desired product, m.p. 280.5°–284° C.

EXAMPLE 29

4-(Methylthio)-imidazo[1,5-d]-as-triazine

To 1.52 gm. of imidazo[1,5-d]-as-triazine-4(3H)-thione in 25 ml. of ethanol is added 0.54 gm. of sodium methoxide. Then 0.63 ml. of methyl iodide is added and the mixture is stirred and heated under reflux for 80 minutes. The mixture is cooled to 0° C. giving a precipitate which is collected. This product is recrystallized from 25 ml. of methanol and treated with charcoal giving the desired product, m.p. 186°–190° C.

EXAMPLE 30

6-Methyl-4-(methylthio)-imidazo[1,5-d]-as-triazine

To a solution of 0.23 gm. of sodium in 10 ml. of methanol is added 1.66 gm. of 6-methyl-imidazo[1,5-d]-as-triazine-4(3H)-thione with warming to produce a solution. The mixture is cooled to room temperature and 0.75 ml. of methyl iodide is added. Cooling overnight gives a solid which is recrystallized from a mixture of 20 ml. of acetone and 6 ml. of ethanol and treated with charcoal. This solid is recrystallized from 20 ml. of ethanol, giving the desired product, m.p. 182.5°–184° C.

EXAMPLE 31

6-n-Propyl-4-(methylthio)-imidazo[1,5-d]-as-triazine

A 3.98 gm. portion of 6-n-propyl-imidazo[1,5-d]-as-triazine-4(3H)-thione is added to a solution of 0.46 gm. of sodium in 15 ml. of methanol under nitrogen. A 1.56 ml. portion of methyl iodide is added. The reaction procedes as described in Example 30 giving the desired product, m.p. 132°–134° C.

EXAMPLE 32

8-Methyl-4-(methylthio)-imidazo[1,5-d]-as-triazine

A 1.66 gm. portion of 8-methyl-imidazo[1,5-d]-as-triazine-4(3H)-thione is added to a solution of 0.23 gm. of sodium in 10 ml. of methanol. A 0.75 ml. portion of methyl iodide is added, the mixture is allowed to stand for 30 minutes and then evaporated to dryness. The product is chromatographed on a silica gel column. The appropriate fractions are recrystallized from acetone giving the desired product, m.p. 128°–129° C.

EXAMPLE 33

6,8-Dimethyl-4-(ethylthio)-imidazo[1,5-d]-as-triazine

The procedure of Example 29 is repeated substituting equimolecular amounts of 6,8-dimethyl-imidazo[1,5-d]-as-triazine-4(3H)-thione and ethyl iodide for the imidazo[1,5-d]-as-triazine-4(3H)-thione and methyl iodide employed in that example. There is thus obtained the title compound in equally good yield.

EXAMPLE 34

6-n-Propyl-8-methyl-4-(isopropylthio)-imidazo[1,5-d]-as-triazine

The general procedure of Example 32 is repeated but replacing the 8-methyl-imidazo[1,5-d]-as-triazine-4(3H)-thione and methyl iodide employed in that example with 6-n-propyl-8-methyl-imidazo[1,5-d]-as-triazine-4(3H)-thione and isopropyl iodide.

EXAMPLE 35

4-(Allylthio)-imidazo[1,5-d]-as-triazine

A 15.2 gm. portion of imidazo[1,5-d]-as-triazine-4(3H)-thione in 75 ml. of methanol is treated with 2.3 gm. of sodium in 75 ml. of methanol. After 5 minutes, a 12.0 gm. portion of allyl bromide is added and the reaction is continued as described in Example 29 giving the desired product, m.p. 68°–69.5° C.

EXAMPLE 36

6,8-Dimethyl-4-(allylthio)-imidazo[1,5-d]-as-triazine

Following the general procedure of Example 35, 6,8-dimethyl-imidazo[1,5-d]-as-triazine-4(3H)-thione is converted to the title compound in equally good yield.

EXAMPLE 37

4-Methylamino-imidazo[1,5-d]-as-triazine

A mixture of 0.96 gm. of 4-imidazolecarboxaldehyde, 2.47 gm. of 3,4-dimethylthiosemicarbazide hydroiodide [E. Cattelain, Bull. Chim. Soc. France, 12, 39 (1945)] in 30 ml. of ethanol is stirred and refluxed for 30 minutes. The reaction mixture is concentrated in vacuum and the residue dissolved in 40 ml. of methanol containing 0.54 gm. of sodium methoxide. After reconcentrating the clear solution is vacuum, 75 ml. of diphenyl ether is added and the mixture heated to 240°–260° C. for 15 minutes. Upon cooling to room temperature, a precipitate forms which is collected and washed with petroleum ether. Recrystallization from 25 ml. of water gives the desired product, m.p. 261°–266° C.

EXAMPLE 38

6-tert-Butyl-4-methylamino-imidazo[1,5-d]-as-triazine

The general procedure of Example 37 is repeated but replacing the 4-imidazolecarboxaldehyde employed in that example with 2-tert-butyl-4-imidazolecarboxaldehyde whereby the title compound is obtained in equally good yield. In like manner, 2-tert-butyl-5-methyl-4-imidazolecarboxaldehyde is converted to 8-methyl-6-tert-butyl-4-methylamino-imidazo[1,5-d]-as-triazine.

EXAMPLE 39

6-n-Butyl-4-ethylamino-imidazo[1,5-d]-as-triazine

The procedure of Example 37 is repeated substituting equimolecular amounts of 2-n-butyl-4-imidazolecarboxaldehyde and 3,4-diethylthiosemicarbazide hydroiodide for the 4-imidazolecarboxaldehyde and 3,4-dimethylthiosemicarbazide hydroiodide employed in that example. There is thus obtained the title compound in equally good yield.

EXAMPLE 40

4-(3-Pyrazolylamino)-imidazo[1,5-d]-as-triazine

A mixture of 6.0 gm. of 4-(methylthio)-imidazo[1,5-d]-as-triazine, 4.15 gm. of 3-aminopyrazole and 150 ml. of toluene is refluxed for 26 hours. The mixture is evaporated and the residue is heated with a mixture of 150 ml. of ethanol and 40 ml. of dimethylformamide. The mixture is cooled to 0° C. and the desired product is collected as a solid, m.p. 271°–274° C.

EXAMPLE 41

4-[(2-Dimethylaminoethyl)amino]-imidazo[1,5-d]-as-triazine

A 5.0 gm. portion of 4-(methylthio)-imidazo[1,5-d]-as-triazine in a mixture of 30 ml. of unsymmetrical dimethylethylenediamine and 20 ml. of toluene is reacted as described in Example 40 giving the desired product as light yellow crystals, m.p. 172°–177° C.

EXAMPLE 42

8-Methyl-4-[(2-diethylaminoethyl)amino]-imidazo[1,5-d]-as-triazine

The procedure of Example 41 is repeated substituting equimolecular amounts of 8-methyl-4-(methylthio)-imidazo[1,5-d]-as-triazine and unsymmetrical diethylethylenediamine for the 4-(methylthio)-imidazo[1,5-d]-as-triazine and unsymmetrical dimethylethylenediamine employed in that example.

EXAMPLE 43

4-(4-Methyl-1-piperazinyl)-imidazo[1,5-d]-as-triazine

A mixture of 0.83 gm. of 4-(methylthio)-imidazo[1,5-d]-as-triazine, 5.0 gm. of N-methylpiperazine and 8 ml. of toluene is reacted as described in Example 40 giving the desired product, m.p. 163°–166° C.

EXAMPLE 44

6-n-Propyl-4-(4-methyl-1-piperazinyl)-imidazo[1,5-d]-as-triazine

Following the general procedure of Example 43, 6-n-propyl-4-(methylthio)-imidazo[1,5-d]-as-triazine is converted to the title compound in equally good yield.

EXAMPLE 45

4-(1-Piperazinyl)-imidazo[1,5-d]-as-triazine

A mixture of 6.5 gm. of 4-(methylthio)-imidazo[1,5-d]-as-triazine, 17.2 gm. of anhydrous piperazine and 120 ml. of toluene is reacted as described in Example 40 giving the desired product, m.p. 160°–165° C.

EXAMPLE 46

3-[(5-Methyl-2-phenyl-4-imidazolyl)methylene]carbazic acid ethyl ester

A mixture of 10.25 gm. of 5-methyl-2-phenyl-4-imidazolecarboxaldehyde and 5.72 gm. of ethyl carbazate in 30 ml. of ethanol containing one drop of acetic acid is boiled for 30 minutes. The mixture is cooled to 0° C. and concentrated under an air stream on a steam bath. A 50 ml. portion of carbon tetrachloride is added and the mixture is cooled to 0° C. overnight. The solid is collected giving the desired product, m.p. 209°–211° C.

EXAMPLE 47

3-[(5-Methyl-2-phenyl-4-imidazolyl)-methylene]-dithiocarbazic acid methyl ester

A 60 gm. portion of 5-methyl-2-phenyl-4-imidazolecarboxaldehyde and 36.8 gm. of methyl dithiocarbazinate are reacted as described in Example 17 giving the desired product, m.p. 180°–185° C.

EXAMPLE 48

8-Methyl-6-phenyl-imidazo[1,5-d]-as-triazine-4(3H)-thione

A mixture of 73.4 gm. of 3-[(5-methyl-2-phenyl-4-imidazolyl)methylene]dithiocarbazic acid methyl ester and 500 ml. of diphenyl ether is reacted as described in Example 23 giving the desired product as purple crystals, m.p. 237.5°–239° C.

EXAMPLE 49

8-Methyl-6-phenyl-imidazo[1,5-d]-as-triazin-4(3H)-one

An 8.33 gm. portion of 3-[(5-methyl-2-phenyl-4-imidazolyl)methylene]carbazic acid ethyl ester in 60 ml. of diphenyl ether is heated in an oil bath at 215°–230° C. for 20 minutes. The reaction mixture is diluted to 400 ml. with petroleum ether. The precipitate is collected and recrystallized from 350 ml. of benzene giving the desired product, m.p. 182°–184.5° C.

EXAMPLE 50

8-Chloro-6-phenyl-imidazo[1,5-d]-as-triazin-4(3H)-one

A 5.0 gm. portion of 6-phenyl-imidazo[1,5-d]-as-triazin-4(3H)-one is mixed with 100 ml. of chloroform on a steam bath while chlorine gas is bubbled through the mixture. A 25 ml. portion of methanol is added. Chlorine is again bubbled through for 10–15 minutes. The mixture is cooled to room temperature, transferred to a separatory funnel, washed with aqueous Na$_2$CO$_3$, aqueous NaHSO$_3$ and finally with water. The mixture is evaporated to 75 ml. on a steam bath, cooled and filtered. The filtrate is evaporated overnight giving a solid. This solid is dissolved in 30 ml. of hot chloroform and filtered. The filtrate is treated with charcoal and isopropanol is added giving the desired product as a solid, m.p. 201°–203° C.

EXAMPLE 51

8-Bromo-6-phenyl-imidazo[1,5-d]-as-triazin-4(3H)-one

A 3.0 gm. portion of 6-phenyl-imidazo[1,5-d]-as-triazin-4(3H)-one is stirred with 100 ml. of chloroform. The mixture is heated slightly and a solution of one ml. of bromine in 10 ml. of chloroform is slowly dripped into the reaction mixture. The mixture is refluxed for 1 hour, cooled to room temperature, and filtered. To the solid is added aqueous Na$_2$CO$_3$ and chloroform and the mixture is shaken in a separatory funnel. The remaining solid and the organic phase are combined and evaporated on a steam bath. Methanol and 2-propanol are added and the mixture is treated twice with charcoal. Cooling gives the desired product as a solid, m.p. 192°–194° C.

EXAMPLE 52

8-Chloro-6-phenyl-imidazo[1,5-d]-as-triazine-4-(3H)-thione

To a solution of 8-chloro-6-phenyl-imidazo[1,5-d]-as-triazine-4(3H)-one (5.84 gm.) in pyridine (100 ml.) is added phosphorus pentasulfide (5 gm.) The mixture is heated at 100° C for 6 hours, filtered hot, and poured into dilute hydrochloric acid. The title product is isolated as a solid.

EXAMPLE 53

8-Bromo-6-phenyl-imidazo[1,5-d]-as-triazine-4(3H)-thione

The procedure of Example 52 is repeated substituting an equimolar amount of 8-bromo-6-phenyl-imidazo-[1,5-d]-as-triazine-4(3H)-one for the 8-chloro-6-phenyl-imidazo[1 5-d]-as-triazine- 4(3H)-one employed in that example. There is thus obtained the title compound.

EXAMPLE 54

8-Methyl-6-phenyl-4-methylthio-imidazo[1,5-d]-as-triazine

The procedure of Example 29 is repeated substituting an equimolar amount of 8-methyl-6-phenyl-imidazo-[1,5-d]-as-triazine-4(3H)-thione for the imidazo[1,5-d]-as-triazine-4(3H)-thione employed in that example. There is thus obtained the title compound in equally good yield.

EXAMPLE 55

8-Chloro-6-phenyl-4-methylthio-imidazo[1,5-d]-as-triazine

The procedure of Example 29 is repeated substituting an equimolar amount of 8-chloro-6-phenyl-imidazo[1,5-d]-as-triazine-4(3H)-thione for the imidazo[1,5-d]-as-triazine-4(3H)-thione employed in that example. There is thus obtained the title compound.

EXAMPLE 56

8-Bromo-6-phenyl-4-methylthio-imidazo[1,5-d]-as-triazine

The procedure of Example 29 is repeated substituting an equimolar amount of 8-bromo-6-phenyl-imidazo[1,5-d]-as-triazine-4(3H)-thione for the imidazo[1,5-d]-as-triazine-4(3H)-thione employed in that example. There is thus obtained the title compound.

EXAMPLE 57

6-Methyl-4-(thiomethyl)imidazo-[1,5-d]-as-triazine.

To a freshly prepared solution of 0.23 g (0.010 g atom) of sodium in 10 ml of methanol is added 1.66 g (0.010 m) of 6-methylimidazo[1,5-d]-as-triazine-4(3H)-thione and the mixture gently warmed until a solution is formed. This solution is cooled to room temperature and 0.75 ml (1.71 g, 0.012 m) of iodomethane is added. After standing overnight, the precipitate which formed is collected. Two recrystallizations from ethanol yield the above-noted desired product, having a melting point equal to m.p. 182.5–184° C.

EXAMPLE 58

4-(Methylthio)-6-propylimidazo[1,5-d]-as-triazine

Employed the method set forth in Example 57 but utilizing 6-propylimidazo[1,5-d]-as-triazine-4(3H)-thione, there is obtained the desired above-noted product having a m.p. = 135.5–137° C.

EXAMPLE 59

8-Methyl-4-(methylthio)imidazo[1,5-d]-as-triazine.

To a solution of 0.23 gm of sodium in 10 ml of methanol is added 1.66 gm of 8-methylimidazo[1,5-d]-as-triazine-4(3H)-thione. Upon obtaining a solution, 0.75 ml (1.71 gm of iodomethane is added. After 0.5 hour, the solution is evaporated and the residue is chromatographed on a silica gel column. Recrystallization from acetone then yields the above-noted desired product having a melting point equal to 128°–128° C.

EXAMPLE 60

6-(Methoxymethyl)-4-(methylthio)-imidazo[1,5-d]-as-triazine

A slurry of 0.98 gm of 6-(methoxymethyl)-imidazo[1,5-d]-as-triazine-4(3H)-thione in 10 ml of N,N-dimethylformamide is treated with 0.28 gm of 50% sodium hydride in oil. Gentle warming is applied until the effervescence stops and then 0.41 ml of iodomethane is added. The resulting precipitate is collected, washed with ether, recrystallized from acetone then ethanol, to yield the above-noted desired product having a melting point equal to 179°–181° C.

EXAMPLE 61

8-Methyl-4-(methylthio)-6-propylimidazo[1,5-d]-as-triazine

Repeating the procedure of Example 59 in every detail except that in lieu of 8-methylimidazo[1,5-d]-as-triazine-4(3H)-thione, 8-methyl-6-propylimidazo[1,5-d]-as-triazine-4(3H)-thione is employed, there is obtained the desired above-noted product having a melting point equal to 74°–78° C (cyclohexane).

This product also possesses herbicidal activity.

EXAMPLE 62

4-(4-Diphenylmethyl-1-piperazinyl)imidazo[1,5-d]-as-triazine

A solution of 6.68 gm of 4-(methylthio)-imidazo[1,5-d]-as-triazine, 15.1 gm of N-diphenylmethylpiperazine and 50 ml of xylene is refluxed for 19 hours. Upon evaporation to dryness, the residue is chromatographed on a silica gel dry column. The product is recrystallized from ethanol and has a melting point equal to 192°–193° C.

EXAMPLE 63

4-Benzylaminoimidazo[1,5-d]-as-triazine

A solution of 16.6 g of 4-(methylthio)imidazo[1,5-d]-as-triazine, 51.3 ml (50.3 g) of benzylamine and 580 ml of toluene is refluxed for 10 days. After cooling, a precipitate is collected and recrystallized from methanol to yield the desired product, m.p. 275°–278° C.

EXAMPLE 64

3-Ethylimidazo[1,5-d]-as-triazine-4(3H)-thione

To a mixture of 3.04 g of imidazo[1,5-d]-as-triazine-4(3H)-thione and 30 ml of methanol is added a solution of 1.08 g of sodium methoxide in 10 ml of methanol. The resulting solution is treated with 1.70 ml (3.28 gm) of iodoethane. Upon evaporation, the residue is purified by preparative thin layer chromatography on silica gel. Recrystallization from acetone gives the desired product, m.p. 143°–144.5° C.

EXAMPLE 65

8-Methyl-4-methylthio-6-phenyl-imidazo[1,5-d]-as-triazine

8-Methyl-6-phenyl-imidazo[1,5-d]-as-triazine-4(3H)-one (4.19 g) is dissolved in 1.5% aqueous sodium bicarbonate. Dimethyl sulphate (1.64 ml, 0.0173 mole) os added at ambient temperature and stirred for 4.5 hours. The solid is removed by filtration and is extracted with methylene chloride (3 × 75 ml). The material, soluble in methylene chloride, is concentrated and chromatographed on silica gel to obtain the product (0.67 g), m.p. 155°–156° C.

Analysis calculated for $C_{13}H_{12}N_4S$: C 60.92; H 4.72; N 21.86; S 12.51. Found: C 61.01; H 4.97; N 21.95; S 11.71.

EXAMPLE 66

Preparation of 50 mg. Tablets

| Per Tablet | | Per 10,000 Tablets |
|---|---|---|
| 0.050 gm. | 8-methyl-6-ethyl-4-(isopropylthio)-imidazo[1,5-d]-as-triazine | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The 8-methyl-6-ethyl-4-(isopropylthio)-imidazo[1,5-d]-as-triazine, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 67

Preparation of Oral Suspension

| Ingredient | Amount |
|---|---|
| 6-ethyl-4-ethylamino-imidazo[1,5-d]-as-triazine | 500 gm. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs to | 100 ml. |

The sorbitol solution is added to 40 ml. of distilled water and the 6-ethyl-4-ethylamino-imidazo[1,5-d]-as-triazine is suspended therewith. The saccharin, sodium benzoate, flavor and dye are added and dissolved. The volume is adjusted to 100 ml. with distilled water. Each ml. of syrup contains 5 mg. of 6-ethyl-4-ethylamino-imidazo[1,5-d]-as-triazine.

EXAMPLE 68

Preparation of Parenteral Solution

In a solution of 700 ml. of propylene glycol and 200 ml. of water for injection is suspended 20.0 grams of 6,8-dimethyl-4-[(2-diethylaminoethyl)amino]-imidazo[1,5-d]-as-triazine hydrochloride with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 69

Preparation of Aerosol Spray

A suspension is prepared of:

| | |
|---|---|
| 6,8-Dimethyl-4-(4-methyl-1-piperazinyl)-imidazo[1,5-d]-as-triazine; micronized (0.5–5.0 microns) | 400 mg. |
| Dichlorodifluoromethane | 100 ml. |
| Sorbitan trioleate | 6.9 mg. |

The active ingredient and sorbitan trioleate are placed in a beaker and the dichlorodifluoromethane is added at −40° C. whereupon a suspension is formed. The mixture is sonified, that is, treated with a Sonifier, manufactured by the Branson Sonic Power Co. of Danbury, Connecticut as model LS-75 at a current input of 9 amperes for two minutes. Additional cold dichlorodifluoromethane is added as necessary to keep the volume at 100 ml. The mixture is uniformly dispersed and has increased stability resulting from the sonification. Each of six 19 ml. stainless steel containers are filled with 15 ml. of the cold mixture, then valves are inserted and sealed in place. On warming, after storage, the 6,8-dimethyl-4-(4 -methyl-1-piperazinyl)-imidazo[1,5-d]-as-triazine remains dispersed and, after merely casual shaking, gives uniform doses of finely divided drug.

We claim:

1. A compound selected from the group consisting of those of the formula:

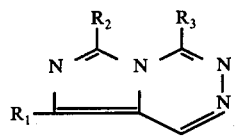

wherein $R_1$ is selected from the group consisting of hydrogen, alkyl having up to 4 carbon atoms, chloro and bromo; $R_2$ is selected from the group consisting of hydrogen, alkyl having up to 4 carbon atoms, methoxymethyl and phenyl; and $R_3$ is selected from the group consisting of allylthio, pyrazolylamino, piperazinyl, 4-methylpiperazinyl and moieties of the formulae: —S—R, —NH—R and

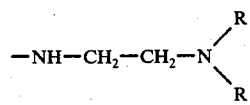

wherein R is alkyl having up to 3 carbon atoms; and the pharmacologically acceptable acid-addition salts thereof when R₃ is a basic nitrogen containing moiety.

2. The compound according to claim 1 wherein R₁ and R₂ are hydrogen and R₃ is methylamino.

3. The compound according to claim 1 wherein R₁ and R₂ are hydrogen and R₃ is 3-pyrazolylamino.

4. The compound according to claim 1 wherein R₁ and R₂ are hydrogen and R₃ is 2-(dimethylamino)ethylamino.

5. The compound according to claim 1 wherein R₁ is methyl, R₂ is ethyl, and R₃ is allylthio.

6. The compound according to claim 1 wherein R₁ is methyl, R₂ is ethyl, and R₃ is n-propylthio.

7. The compound according to claim 1 wherein R₁ is hydrogen, R₂ is isopropyl, and R₃ is ethylamino.

8. The compound according to claim 1 wherein R₁ and R₂ are methyl and R₃ is piperazinyl; as the hydrochloride salt.

9. The compound according to claim 1 wherein R₁ is methyl, R₂ is n-butyl, and R₃ is 4-methylpiperazinyl; as the hydrobromide salt.

10. The compound according to claim 1 wherein R₁ and R₂ are hydrogen and R₃ is 2-(di-n-propylamino)ethylamino.

11. The compound according to claim 1 wherein R₁ and R₂ are ethyl and R₃ is allylthio.

12. The compound according to claim 1 wherein R₁ is chloro, R₂ is phenyl, and R₃ is 2-(diethylamino)ethylamino.

13. The compound according to claim 1 wherein R₁ is bromo, R₂ is n-butyl, and R₃ is isopropylthio.

14. The method of lowering elevated blood pressure in a mammal which comprises administering internally to said mammal an effective amount of a compound selected from the group consisting of those of the formula:

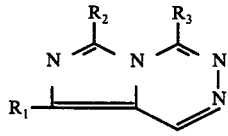

wherein R₁ is selected from the group consisting of hydrogen, alkyl having up to 4 carbon atoms, chloro and bromo; R₂ is selected from the group consisting of hydrogen, alkyl having up to 4 carbon atoms, methoxymethyl and phenyl; and R₃ is selected from the group consisting of allylthio, pyrazolylamino, piperazinyl, 4-methylpiperazinyl and moieties of the formulae:
—S-R, —NH-R and

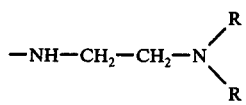

wherein R is alkyl having up to 3 carbon atoms; and the pharmacologically acceptable acid-addition salts thereof when R₃ is a basic nitrogen containing moiety.

15. A therapeutic composition in dosage unit form useful for lowering elevated blood pressure in mammals comprising from about 1.0 mg. to about 25.0 mg. per kg. of body weight per daily dosage unit, in association with a pharmaceutical carrier, of a compound selected from the group consisting of those of the formula:

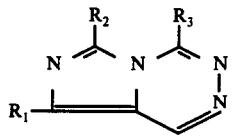

wherein R₁ is selected from the group consisting of hydrogen, alkyl having up to 4 carbon atoms, chloro and bromo; R₂ is selected from the group consisting of hydrogen, alkyl having up to 4 carbon atoms, methoxymethyl and phenyl; and R₃ is selected from the group consisting of allylthio, pyrazolylamino, piperazinyl, 4-methylpiperazinyl and moieties of the formulae:
—S-R, —NH-R and $$-NH-CH_2-CH_2-N\begin{matrix}R\\ \\R\end{matrix}$$

wherein R is alkyl having up to 3 carbon atoms; and the pharmacologically acceptable acid-addition salts thereof when R₃ is a basic nitrogen containing moiety.

16. The process of preparing compounds of the formula:

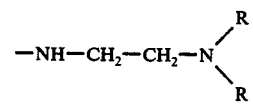

wherein R₁ is hydrogen, alkyl having up to 4 carbon atoms, chloro or bromo; R₂ is hydrogen, alkyl having up to 4 carbon atoms or phenyl; and R is allyl or alkyl having up to 3 carbon atoms which comprises contacting a compounds of the formula:

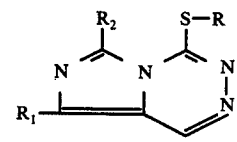

wherein R₁ and R₂ are as hereinabove defined with allyl bromide or an alkyl iodide having up to 3 carbon atoms in a lower alkanol solvent at from ambient to the reflux temperature thereof for a period of time sufficient for a substantial degree of displacement to occur.

17. The process of preparing compounds of the formula:

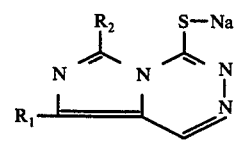

wherein R₁ is hydrogen, alkyl having up to 4 carbon atoms, chloro or bromo; R₂ is hydrogen, alkyl having up to 4 carbon atoms or phenyl; and R is alkyl having up to 3 carbon atoms which comprises heating a compound of the formula:

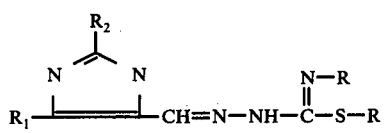

wherein R, $R_1$, and $R_2$ are as hereinabove defined in a non-polar high boiling organic solvent at a temperature of 225°–275° C. for a period of time sufficient for a substantial degree of ring closure to occur.

18. The process of preparing compounds of the formula:

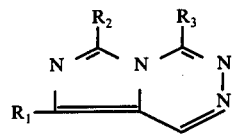

wherein $R_1$ is hydrogen, alkyl having up to 4 carbon atoms, chloro or bromo; $R_2$ is hydrogen, alkyl having up to 4 carbon atoms or phenyl; and $R_3$ is pyrazolylamino, piperazinyl, 4-methylpiperazinyl or a moiety of the formula:

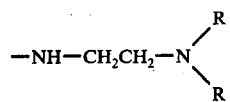

wherein R is alkyl having up to 3 carbon atoms which comprises contacting a compound of the formula:

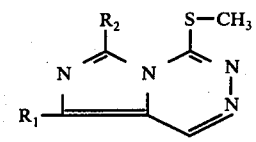

wherein $R_1$ and $R_2$ are as hereinabove defined with 3-amino-pyrazole, piperazine, 4-methylpiperazine or an amine of the formula:

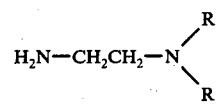

wherein R is as hereinabove defined, at 80°–125° C. in an inert solvent for a period of time sufficient for a substantial degree of displacement to occur.

* * * * *